(12) United States Patent
Schmitt

(10) Patent No.: US 7,396,161 B2
(45) Date of Patent: Jul. 8, 2008

(54) METHOD FOR GENERATING AN X-RAY IMAGE OF AN EXTREMITY OF A PATIENT WITH A SCALE OF LENGTH

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 64 days.

(21) Appl. No.: 11/529,636

(22) Filed: Sep. 28, 2006

(65) Prior Publication Data

US 2007/0071175 A1 Mar. 29, 2007

(30) Foreign Application Priority Data

Sep. 29, 2005 (DE) .................. 10 2005 046 764

(51) Int. Cl.
*H05G 1/00* (2006.01)
*G01D 18/00* (2006.01)

(52) U.S. Cl. ...................... 378/204; 378/207

(58) Field of Classification Search ......... 378/204–207, 378/210

See application file for complete search history.

(56) References Cited

U.S. PATENT DOCUMENTS 5,606,590 A * 2/1997 Petersen et al. ............ 378/177
6,398,408 B1 * 6/2002 Polkus ....................... 378/207
6,731,718 B2 * 5/2004 Ogura et al. ................. 378/63
6,792,071 B2   9/2004 Dewaele
6,821,017 B1 * 11/2004 Tankersley .................. 378/207
7,203,277 B2 * 4/2007 Birkenbach et al. ........ 378/98.5
2005/0007387 A1   1/2005 Abe et al.

FOREIGN PATENT DOCUMENTS

DE    31 28 380 A1    2/1983
DE    101 60 532 C1   6/2003
EP    1 349 098 A1    10/2003

* cited by examiner

*Primary Examiner*—Irakli Kiknadze

(57) ABSTRACT

In an X-ray installation comprising an X-ray source, a patient support, an X-ray detector and an electronic evaluation system, a distance is determined from an extremity of a patient which is to be imaged to the X-ray detector and is made available as an electronic data value to the electronic evaluation system. If the distance from the X-ray source to the X-ray detector as an electronic data value is also known, then a scale can be calculated for the X-ray image from the two distances on the basis of the imaging laws for the generation of the X-ray image, which scale can be faded into the X-ray image or else electronically assigned to this image for an interrogation of coordinates.

13 Claims, 3 Drawing Sheets

METHOD FOR GENERATING AN X-RAY IMAGE OF AN EXTREMITY OF A PATIENT WITH A SCALE OF LENGTH

CROSS REFERENCE TO RELATED APPLICATIONS

This application claims priority of German application No. 10 2005 046 764.4 DE filed Sep. 29, 2005, which is incorporated by reference herein in its entirety.

FIELD OF INVENTION

The invention relates to a method for generating an X-ray image of an extremity of a patient with a scale of length. It also relates to a light-source device which is used in such a method, as well as, in general, to an X-ray installation. Finally, the invention also relates to a patient support for an X-ray installation.

BACKGROUND OF THE INVENTION

Full information from an X-ray image can include absolute values of the lengths of extremities of a patient being known. Such absolute data can be indispensable, particularly in the planning of an operation.

A lead ruler has been used until now to provide a scale of length. The lead ruler is arranged next to the patient or else fastened to him/her and is also reproduced on the X-ray image. In particular, fastening the lead rule to the patient is laborious and costly and requires the cooperation of the patient. The use of a lead ruler also has the disadvantage that it is difficult to compile multiple images and then determine lengths covering all the images. If therefore lengths are to be derived from the images, recordings of the whole extremity are made at once over a large area, e.g. whole-leg recordings using a film cassette which is 90 or 120 cm long.

From DE 31 28 380 A1, an X-ray diagnostic installation for X-ray tomographic images is known. Certain layers of a patient lying on a patient table are especially highlighted by an X-ray image. In order to calculate the enlargement, a layer height computer is provided which uses the geometric data for the tomograph as an input variable. A marking for the dimensions in the layer plane can be faded into the image. The geometric data for the tomograph is displayed as given and does not have to be measured specifically.

From US 2005/0007387 A1 a device, method and program for the graphical representation of X-ray images are known, wherein in an embodiment for defining an image enlargement the intercept theorems are used. It is not disclosed how the input variables for the intercept theorems are determined.

In DE 101 60 532 C1, a method and a device are known for the three-dimensional locating of an object in a body. The focus of interest is on determining the vertical position of the object. Instead of using a ruler, the object is displaced around a displacement path and the projection of the displacement path determined in an X-ray image. From the intercept theorems, the vertical position of the object can be determined with the aid of the displacement path and the projection and the distance of the radiation source for the X-ray image from the image plane of the projection image.

From EP 1 349 098 A1 and U.S. Pat. No. 6,792,071 B2 methods are known for performing geometric measurements on digital radiological images, in which so-called graphical templates are used. These templates also incorporate as geometric parameters the distances between X-ray source, patient and detector.

SUMMARY OF INVENTION

The object of the invention is to indicate a way in which, in dispensing with a lead ruler, a scale of length can be provided electronically, based, to be precise, on a measurement to be carried out as simply as possible of the distance from the extremity of the patient to the X-ray detector.

According to a first alternative of the invention, a method is provided as claimed in the first independent claim. According to this, in an X-ray installation comprising an X-ray source, a patient presentation support (i.e. a location in which the patient is placed in position, that is stands or lies), an X-ray detector and an electronic evaluation system, a patient is firstly brought to the patient presentation support. Independently thereof, the distance from the X-ray source to the X-ray detector is communicated to the electronic evaluation system as an electronic data value. Then, a distance is determined from the extremity of the patient to the X-ray detector and is provided to the electronic evaluation system as an electronic data value. With the position of the patient unchanged, an X-ray image is recorded with the aid of the X-ray source and the X-ray detector. Then, a scale can be calculated for the X-ray image in the electronic evaluation system with the aid of the electronic data values for the two distances. The calculation is based essentially on the use of the intercept theorems on the path from the X-ray source via the extremity to the X-ray detector.

As a result, the scale in the electronic evaluation system is available electronically. It can then be assigned to the X-ray image display. The assignment can appear such that the scale is simply faded into the displayed X-ray image. Alternatively, a system of coordinates can be assigned to the X-ray system. If a datapoint is then interrogated, for example by clicking with a mouse on a point on the displayed X-ray image, then a scale value can be displayed numerically. Preferably, two coordinate points in the system of coordinates are clicked on, and the distance between the two points is output according to the scale.

The invention uses the imaging laws in an X-ray representation, such as the intercept theorems. While the distance from the X-ray source to the X-ray detector will generally be constant or can easily be made available by the control as an electronic data value, measurement of the distance from the extremity of the patient to the X-ray detector presents the real challenge.

In the first alternative, the distance of the extremity of the patient from the X-ray detector is determined as follows: A light-source device, stationary in relation to the X-ray detector, is provided on the patient presentation support. This is intended to comprise a displaceable light source, preferably one that is displaceable in a direction perpendicular to the plane of representation of the X-ray image. An electronic data value for the displacement setting of the light source, i.e. for the position of the light source in the light-source device should be determinable or be available electronically. Since the light-source device as a whole is stationary in relation to the X-ray detector, the distance from the light source to the X-ray detector can thus be determined electronically.

The light source is now switched on and is displaced until the light beam shines on to the extremity of the patient. In the relevant displacement position, the displacement setting is determined, and it is available in the electronic evaluation system. A distance from the extremity of the patient to the X-ray detector can then be assigned in the electronic evaluation system to the displacement position. When the displaceable light source shines perpendicularly in the imaging plane laterally on to the patient, then the distance from the light source to the X-ray detector is equal to the distance from the extremity of the patient to the X-ray detector.

Naturally, a large-area light source cannot be used, but a light source which emits a considerably restricted beam in at least one direction can. Preferably, a light source is used which emits a line-shaped light beam. The light source can then also be rotatably fashioned, whereby its angular position should be electronically determinable and should be available to the electronic evaluation system as an electronic data value. A possible inclination of the extremity of the patient can then be determined by rotating the light source until the entire line-shaped beam shines onto the extremity. The inclination of the extremity can then, in the manner described above, be taken into account in calculating the scale. Instead of a line-shaped light beam, a light (beam) point sequence can also be used (which can also be rotatably fashioned). It is not therefore necessary for a line to be formed in a spatially unbroken manner, but breaks can be provided between the individual parts of the light beam (the individual points). In the limiting case, two light points suffice, whereby the light source should then if possible be rotatably fashioned.

The light source will typically be a laser, i.e. in the present case preferably a rotatable line laser.

Using the above-mentioned light source, it is possible to determine both the (average) distance of the extremity of the patient from the X-ray detector and the inclination of the extremity perpendicular to the imaging plane. This can be taken into account in calculating and/or assigning the scale. An inclination of the extremity perpendicular to the imaging plane results in the extremity together with various of its parts belonging to different imaging planes. Ideally, linearizing is carried out here, i.e. on the finished image it is assumed that the scale is compressed according to the sine value of the angle of inclination. If the extremity is inclined in the imaging plane, then this will have to have an effect, in particular, when the scale is drawn in, for the scale should be represented alongside the extremity so that if the extremity is inclined, the scale must also be shown inclined on the finished X-ray image.

Where the inclination of the extremity in the imaging plane is now also to be determined, a further light beam from the front, which also emits a line-shaped profile, can be used for this purpose.

It is preferable at the height of the X-ray source (10), in particular of a collimator in an X-ray source, for a further light source, in particular a laser, to be provided which emits a line-shaped light beam, which is rotatable and whose angular position is available electronically to the electronic evaluation system. The further light source is then rotated until the entire line-shaped beam shines onto the extremity. The angular position of the further light source is taken into account when a scale is faded into the X-ray image to the extent that this scale copies the inclination. By "copying" is meant here that the faded-in scale is inclined equally as much as the extremity.

In the invention, an operator has to control the line laser such that the line profile shines precisely onto the inclined extremity. From the settings relating to the light sources, the distance and the inclination are then inferred.

In an alternative of the inventive method as claimed in the second independent claim, these variables are to a certain extent determined automatically: A camera is provided stationary relative to the X-ray detector, which camera photographs the extremity of the patient. It is connected to an electronic evaluation system which evaluates the camera image with the aid of image recognition algorithms and calculates the distance of the extremity of the patient from the X-ray detector on the basis of the distance of the camera from the X-ray detector and the imaging laws which apply to the camera. In other words, the evaluation system recognizes the extremity in the image, knows the distance of the camera from the X-ray detector and can then, based on the imaging laws of the camera, also calculate the distance of the extremity of the patient from the X-ray detector. Of course, this camera can also determine the inclination of the extremity. Also, a second inclination of the extremity (in the imaging plane) can be determined here by a second camera recording an image of the extremity essentially from the direction of the X-ray source in order to capture automatically, through automatic image evaluation in an electronic evaluation system, a possible inclination of the extremity.

To realize the first alternative, which uses a light source comprising a line-shaped light beam in profile, the invention provides a light-source device comprising: a light source which emits a line-shaped light beam profile, and the light source being displaceable along a bar, an electronic data value being provided which expresses the displacement setting. The light source is rotatable perpendicularly to the direction of light irradiation, and an electronic data value is provided which expresses the angle of rotation.

Such a light-source device is consequently tailor-made for the inventive method. Here, too, the light source can again be a line laser. The electronic data values can be activation signals for activating motors for displacing and/or rotating the light source. In particular, in the above method, an electronic data value is to be interpreted as being available even if it is not a measurement value but an activation signal.

In order to make the focusing of the light beam on the extremity of the patient simpler, it is appropriate to fit a housing of the device with a reflecting surface, the light emerging from the surface (i.e. from a slot in the surface). An operator does not therefore need to look directly at the extremity of the patient, but can also be guided by the reflected image on the light-source device.

The invention also relates to an X-ray installation comprising an X-ray source, a patient presentation support, an X-ray detector and an electronic evaluation system. A light-source device of the above-mentioned type is provided which is stationary in relation to the X-ray detector, the electronic data values being available to the electronic evaluation system. Here, "being available" can again also be understood as meaning that the electronic evaluation system activates motors in the light-source device by means of the activation signals. The electronic evaluation system is designed in particular for calculating a scale of length from the electronic data values and further data stored in the electronic evaluation system (distance of X-ray source from the X-ray detector, etc.).

The X-ray installation can, as an alternative to the stationary light-source device, comprise an electronic camera, stationary relative to the X-ray detector, the electronic evaluation system being designed for evaluating automatically by means of image evaluation algorithms images recorded by the camera. Here, too, the electronic evaluation system is designed for calculating a scale of length, in the present case on the basis of information obtained from the images.

Since in the case of the present X-ray installations and of the inventive method, the stationary positioning of the light-source device relative to the X-ray detector or of the camera relative to the X-ray detector plays an essential role, the present invention also includes a novel patient support on which a patient for presentation can stand for X-ray imaging (i.e. when X-ray imaging is carried out). The patient support has an adapter base, and by means of the adapter base he/she can be conveyed to a stationary position relative to an x-ray detector support and thus to an X-ray detector (mounted on the X-ray detector support). The light-source device or the electronic camera can then be fastened in a stationary position on the patient support, but also on the X-ray detector support.

The adapter base can be designed in particular such that a form-closed connection to a component part of the X-ray detector support is established, so that the distance from the patient support to the X-ray detector mounted on the X-ray detector support is predefined and thus known.

BRIEF DESCRIPTION OF THE DRAWINGS

A preferred embodiment of the invention will now be described with reference to the drawings, in which:

FIG. 4A shows three different X-ray images, which in FIG. 4B are viewed combined into one X-ray image, a scale of length being faded in.

DETAILED DESCRIPTION OF THE INVENTION

Figure 1:
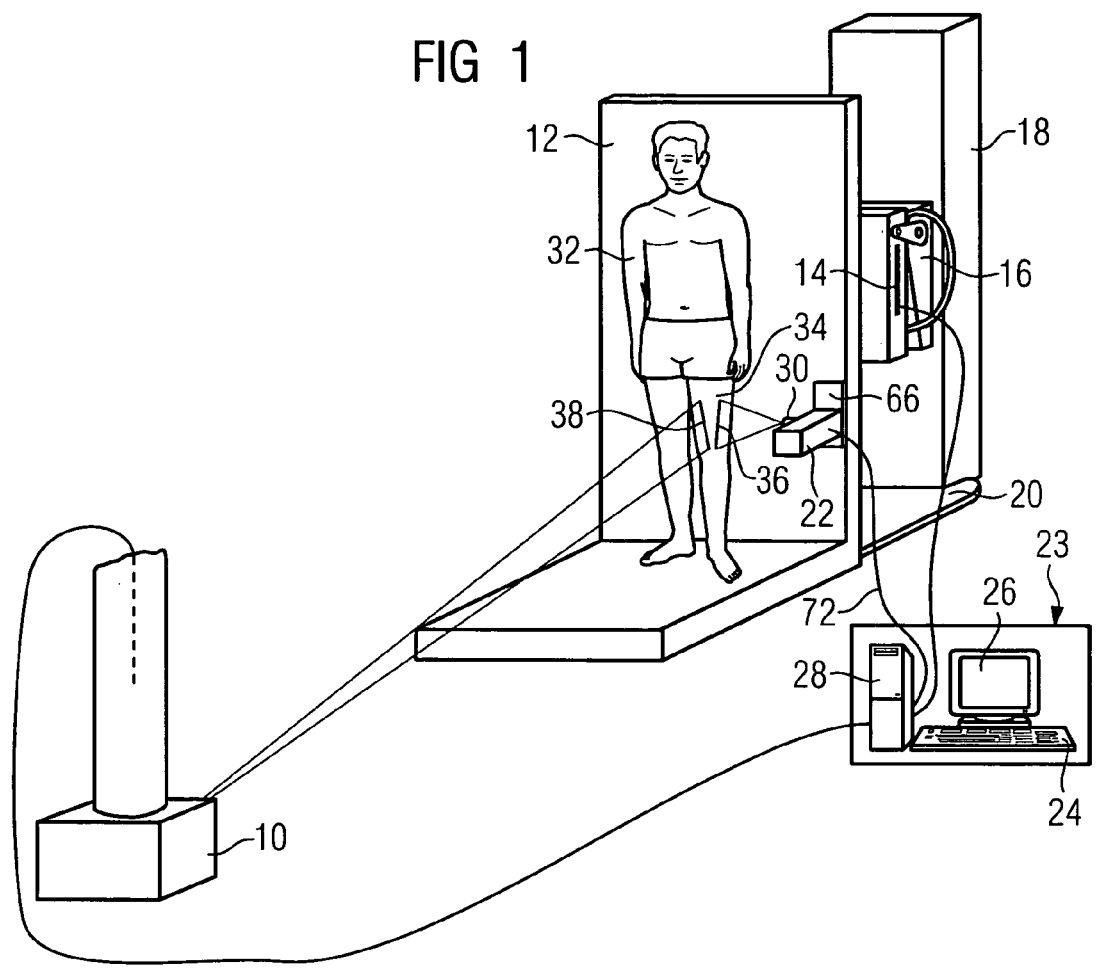
FIG. 1 shows an X-ray installation according to the invention for implementing the method according to the invention.

FIG. 1 shows an X-ray installation according to the invention. It comprises an X-ray source 10, a patient support 12 as a patient presentation support and an X-ray detector 14. The X-ray detector 14 is located in a holder 16 which is displaceable on an X-ray detector support 18. The patient support 12 stands not only simply in front of the X-ray detector support 18 but is arranged in a defined manner stationary in relation to this X-ray detector support. An adapter base 20 defines the distance from the patient support to the X-ray detector support and thus the distance from the patient support 12 to the X-ray detector 14.

Figure 3A:
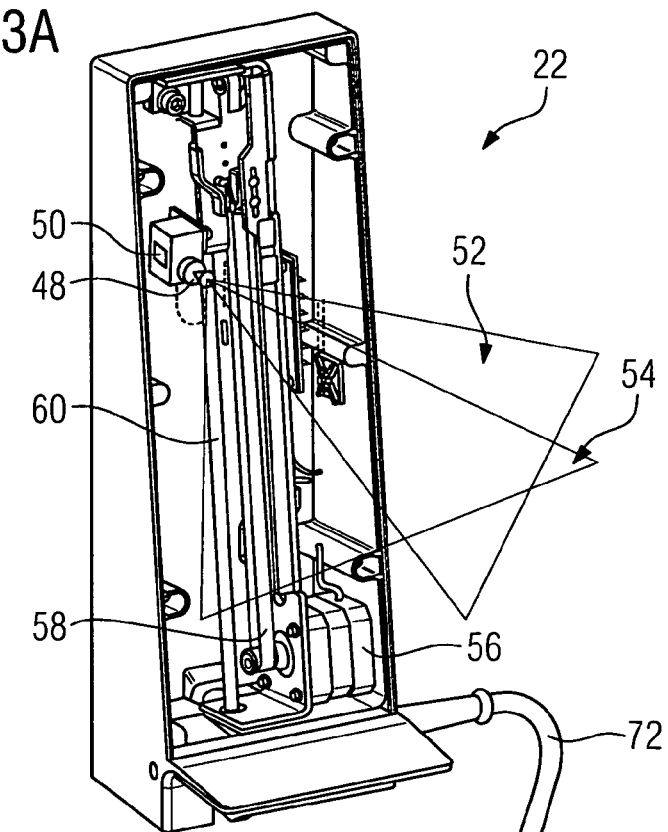
FIG. 3A shows an interior view of a light-source device according to the invention.

Standing in a stationary position relative to the patient support 123 is a light-source device 22, which will be described in greater detail later with reference to FIGS. 3A and 3B. The light-source device 22 can be vertically displaceable, but its distance from the X-ray detector 14 is defined and fixed.

Furthermore, part of the X-ray installation according to the invention is an electronic evaluation system which here is labeled 23 in its entirety. The electronic evaluation system 23 comprises a user interface (keyboard) 24, at least one display screen (26) on which the X-ray images recorded by the X-ray detector 14 can be displayed, and, as the principal item, a computer unit 28.

The electronic evaluation system 23 is in particular also suitable for activating the light-source device 22. In the light-source device 22 there is namely provided a light source 30 which is displaceable in a longitudinal direction, i.e. perpendicularly to the imaging plane. The light source is a line laser which, in addition, is rotatable. The electronic evaluation system 23 can emit control signals for displacing and for rotating the light source 30. Information about the setting of the light source 30 is thus available to the electronic evaluation system. Since on the one hand the patient support 12 is by means of the adapter base 20 stationary relative to the detector 14 and on the other hand the light-source device is mounted in a stationary position on the patient support 12, this information about the setting of the light source 30 in the light-source device 22 corresponds to information about the distance of the light source 30 from the X-ray detector and about its relative orientation in relation to this detector.

In the method according to the invention, a patient 32 is now requested, in order to prepare an image reproduction, to stand on the patient support 12. He/she adopts a comfortable position as he/she intends to adopt in the subsequent X-ray recording. The present concern is to fade a scale of length into an X-ray image to be recorded. To this end, the distance d between the patient extremity 34 and the detector 14 has to be determined (cf. FIG. 2). A user now uses the electronic evaluation system 23 to activate the light source 30. The light source 30 is switched on and the operator displaces the light source 30 until a light beam 36 which is emitted by the light source 30 lands on the center of the extremity 34 of the patient 32 which is to be imaged. Then, by rotating the light source, the light beam 36 from the light source 30 is rotated on the extremity 34 and brought to the position shown in FIG. 1, in which position the light beam 36 extends in its longitudinal extension precisely along the extremity 34. This can also be seen schematically in the side elevation according to FIG. 2. Independently of this light beam, a further light beam is emitted from the height of the X-ray source 10. To this end, a further line laser is provided on the plane of the collimator in the X-ray source 10. The line laser in the X-ray source is also meant to be rotatable. It is rotated until the light beam 38 of the further laser also extends along the extremity 34 of the patient 32. In the status shown in FIG. 1, the settings of the light source 30 are now registered and, in addition, the inclination of the further laser in the X-ray source 10 determined with the light beam 38. An X-ray image is then recorded, with the position of the patient 32 unchanged.

Figure 2:
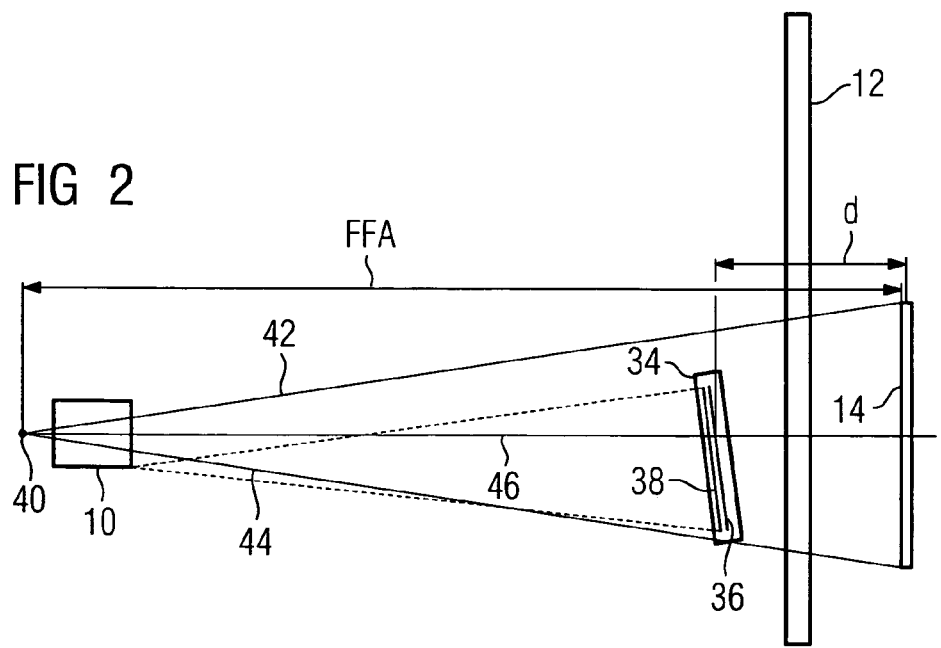
FIG. 2 illustrates the beam path in the X-ray installation according to FIG. 1 viewed from the side.

The electronic evaluation system 23 now knows: the distance d of the extremity 34 from the X-ray detector 14 (see FIG. 2), the inclination of the extremity 34 perpendicularly to the imaging plane (inclination of the beam 36) and the inclination of the extremity in the imaging plane (inclination of the beam 38). Furthermore, the film-focus distance (FFA), i.e. the distance from the X-ray source 10 to the X-ray detector 14, expressed by the distance from the virtual focus of the X-ray source to the detector plane, is already known in advance to the electronic evaluation system. Based upon simple projection geometry, it can now be calculated how the extremity 34 will be mapped in an enlarged manner on the detector 14. FIG. 2 illustrates to this end the path of the X-radiation from the focus 40 behind the X-ray source 10 (virtual source) to the detector 14 with the outer rays 42 and 44 and the central ray 46. The rays otherwise shown in FIG. 2 are the rays of the laser arranged in the X-ray source 10 for generating the light beam 38. Not to be seen in the side elevation is the beam path from the light source 22 to the extremity 34; only the line-shaped beam 36 is shown.

It should be pointed out once again that the beam 36 does not come to lie precisely on the extremity 34 immediately once the line laser is switched on. The light-source device 22 shown in FIG. 3a is provided. A laser 48 is arranged in it. Located behind the laser is a rotational motor 50 for rotating the laser. Two light irradiation possibilities are shown, a beam 52 and a beam 54. An adjustable motor 56 is provided for this purpose which turns a toothed belt 58 which can move the laser 48 together with the motor 50 along a guide rod 60.

Figure 3B:
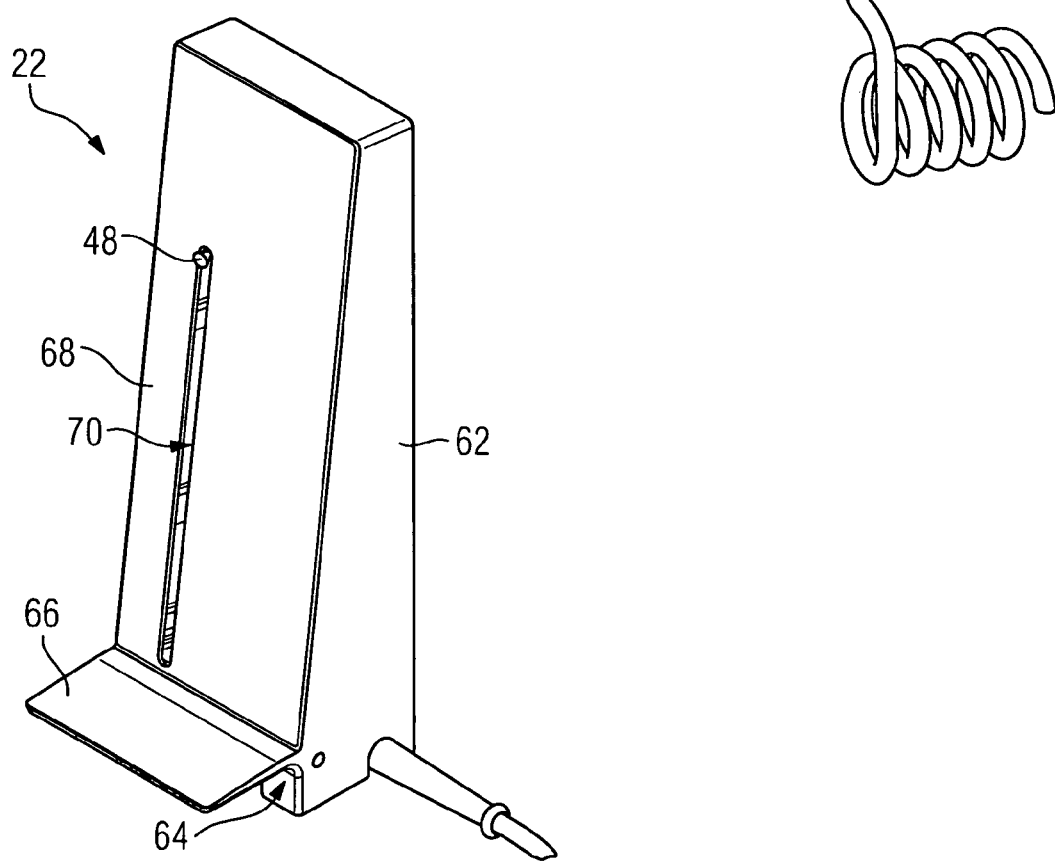
FIG. 3B shows an exterior view of the light-source device according to FIG. 3A.

The housing 62 of the device 22 is, as can be seen in FIG. 3B, designed in its basal region 64 to fasten the light-source device 22 to a patient support in the manner of the patient support 12. Here, a plate 66 serves as the stop. The plate 66 will as a general rule come to lie against a support structure of the patient support 12 so that the light-source device 66 can, as such, be fastened stationary relative to the patient support.

The surface from which the light beam 52 or 54 of the laser 48 emerges comprises a surface plate 68 with a slot 70 in which the laser 48 can move when moving along the rod 60. The surface plate 68 is fashioned in particular in a reflecting manner. An operator can, when he/she displaces the laser 48 in a longitudinal direction or rotates the laser, observe the extremity 34 of the patient on the reflecting surface 68 and does not have to glance between the device 22 and the extremity 34.

To supply the control signals, a line 72 is provided.

Figure 4A:
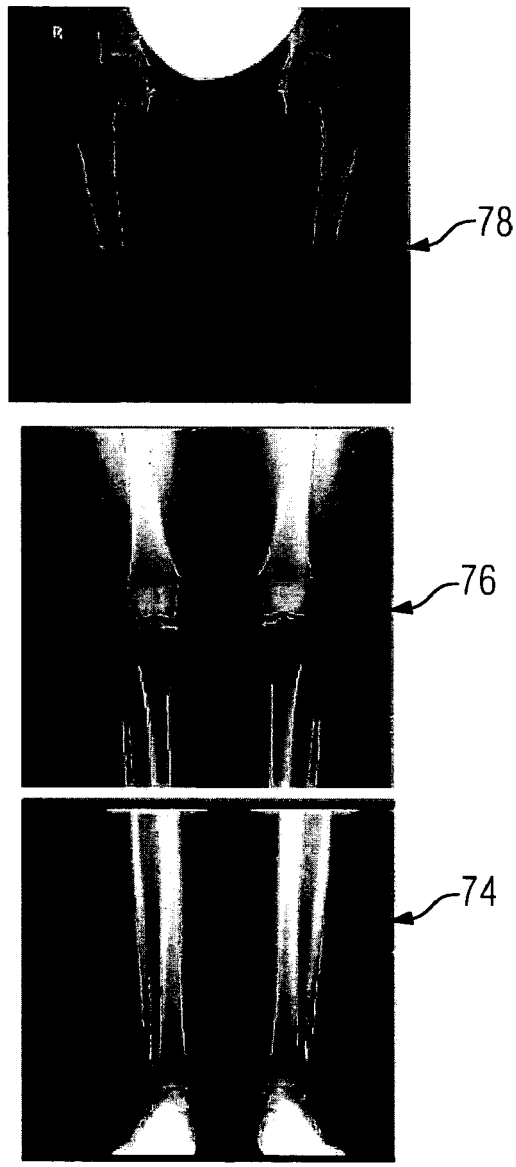

As mentioned above, the electronic evaluation system 23 can fade a scale automatically into a recorded X-ray image. In addition, this is also possible when the X-ray image has been combined from a variety of different X-ray images. FIG. 4A shows three X-ray images 74, 76, 78 which are combined in accordance with FIG. 4B into a single X-ray image. Appropriate techniques for combining individual X-ray images are known in the prior art and are based on automatic image recognition in the electronic evaluation system 23. Since, according to the invention, a scale is assigned to each individual X-ray image 74, 76 and 78, in accordance with FIG. 4B an overall scale can be assigned to the overall image. This is illustrated schematically by the fading in of the numerals 01 and 9 and 10. The inclination of the scale matches the inclination of the leg reproduced on the right hand side because the laser at the X-ray source 10 (with light beam 38 in FIG. 1) has determined a corresponding inclination of the right leg.

Figure 4B:
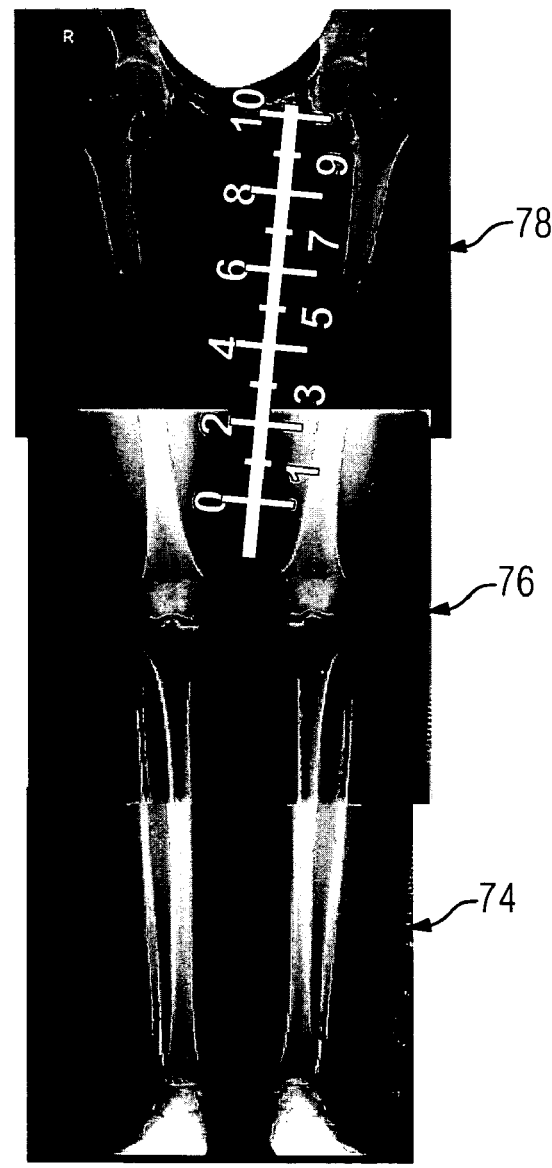

In FIG. 4B, a constant scale is assumed across the two partial images 78 and 76. If, due to a pronounced inclination of the patient, these scales should by chance deviate from one another in the individual images 76 and 78, then it is simply possible to draw in a divided ruler over the images 76 and 78 which allows for this, i.e. which traces the change in scale.

The ease of operability of the light-source device 22 and of the laser at the X-ray source 10 contrasts pleasantly with the awkwardness of working with rulers in the prior art. An advantage of the embodiment shown is that an operator continues as before to work on the spot, ensuring exact measurement of the distance from the extremity to the X-ray detector. In an alternative embodiment, instead of the light-source device 22, a camera automatically recording an image perpendicularly to the X-ray imaging plane is used. Based upon image recognition algorithms, the distance between the extremity and the X-ray detector is then calculated. Here, too, it is important for the camera on the patient support to be connected in a stationary manner to the X-ray detector.

The invention claimed is:

1. A method for generating an X-ray image of an extremity of a patient with a scale of length, comprising:
    locating the patient in a patient presentation area adapted to facilitate the X-ray image;
    arranging an X-ray source and an X-ray detector between the patient;
    determining a first distance measured from the X-ray source to the X-ray detector;
    communicating the first distance to an electronic evaluation system as a first electronic data value;
    determining a second distance measured from the extremity to the X-ray detector via a light-source device arranged stationary in relation to the X-ray detector, the light-source device comprising a displaceable light source having an electronically determinable distance from the X-ray detector, the light source switched on and displaced until the light beam shines on to the extremity;
    communicating the second distance to the electronic evaluation system as a second electronic data value;
    calculating a scale for the X-ray image via the first and second electronic data values via an electronic evaluation system;
    recording an X-ray image via the X-ray source and the X-ray detector while keeping the position of the patient unchanged; and
    associating the calculated scale with the X-ray image.

2. The method as claimed in claim 1, wherein the light source is rotatable and emits a line-shaped light beam or a light point sequence.

3. The method as claimed in claim 2, wherein an angular position of the light source is determined and made available to the electronic evaluation system in order to determine a possible inclination of the extremity by rotating the light source until the entire line-shaped beam or the light point sequence shines onto the extremity.

4. The method as claimed in claim 3, wherein the inclination of the extremity is taken into account in calculating or associating the scale.

5. The method as claimed in claim 1, wherein the light source is a rotatable line laser.

6. The method as claimed in claim 1, comprising a further rotatable light source that emits a line-shaped light beam or a light point sequence, the second light source rotated until the entire line-shaped beam or the entire light point sequence shines on the extremity, and an angular position of the second rotatable light source is taken into account when the scale is faded into the X-ray image with the effect that the faded scale simulates the inclination.

7. The method as claimed in claim 1, wherein the patient presentation area comprises a patient support on which a patient stands during the X-ray imaging, the patient support adapted to attain a stationary position relative to an X-ray detector support.

8. A method for generating an X-ray image of an extremity of a patient with a scale of length, comprising:
    locating the patient in a patient presentation area adapted to facilitate the X-ray image;
    arranging an X-ray source and an X-ray detector between the patient;
    determining a first distance measured from the X-ray source to the X-ray detector;
    communicating the first distance to an electronic evaluation system as a first electronic data value;
    determining a second distance measured from the extremity to the X-ray detector via a camera arranged stationary in relation to the X-ray detector, the camera having an electronically determinable distance from the X-ray detector;
    communicating the second distance to the electronic evaluation system as a second electronic data value;
    calculating a scale for the X-ray image via the first and second electronic data values via an electronic evaluation system;
    recording an X-ray image via the X-ray source and the X-ray detector while keeping the position of the patient unchanged; and
    associating the calculated scale with the X-ray image.

9. The method as claimed in claim 8, wherein an angular position of the camera is determined and made available to the electronic evaluation system in order to determine a possible inclination of the extremity.

10. The method as claimed in claim 9, wherein the inclination of the extremity is taken into account in calculating or associating the scale.

11. The method as claimed in claim 8, comprising a further rotatable camera having an angular position that is taken into account when the scale is faded into the X-ray image with the effect that the faded scale simulates the inclination.

12. The method as claimed in claim 8, wherein a further camera records an image of the extremity in order to determine a possible inclination of the extremity in the X-ray imaging plane, the inclination taken into account in the calculation or associating of the scale.

13. The method as claimed in claim 8, wherein the patient presentation area comprises a patient support on which a patient stands during the X-ray imaging, the patient support adapted to attain a stationary position relative to an X-ray detector support.

* * * * *